(12) United States Patent
Stefano

(10) Patent No.: US 6,297,010 B1
(45) Date of Patent: Oct. 2, 2001

(54) METHOD FOR DETECTING AND IDENTIFYING MUTATIONS

(75) Inventor: James E. Stefano, Hopkinton, MA (US)

(73) Assignee: Genzyme Corporation, Framingham, MA (US)

(*) Notice: Subject to any disclaimer, the term of this patent is extended or adjusted under 35 U.S.C. 154(b) by 0 days.

(21) Appl. No.: 09/016,542

(22) Filed: Jan. 30, 1998

(51) Int. Cl.⁷ .............................. C12Q 1/68; C12P 19/34

(52) U.S. Cl. ........................ 435/6; 435/91.1; 435/91.2

(58) Field of Search ........................... 435/6, 91.1, 91.2

(56) References Cited

U.S. PATENT DOCUMENTS

| | | | |
|---|---|---|---|
| 5,217,863 | 6/1993 | Cotton et al. | 435/6 |
| 5,412,087 | * 5/1995 | McGall et al. | 536/24.3 |
| 5,436,142 | 7/1995 | Wigler et al. | 435/91.2 |
| 5,459,039 | 10/1995 | Modrich et al. | 435/6 |
| 5,501,964 | 3/1996 | Wigler et al. | 435/91.2 |

FOREIGN PATENT DOCUMENTS

| | | |
|---|---|---|
| WO 93/02216 | 2/1993 | (WO). |
| WO 93/20233 | 10/1993 | (WO). |
| WO 93/22462 | 11/1993 | (WO). |
| WO 95/12689 | 5/1995 | (WO). |
| WO 95/29258 | * 11/1995 | (WO). |
| WO 95/29251 | 11/1995 | (WO). |
| WO 95/35505 | 12/1995 | (WO). |
| 96/41002 | * 12/1996 | (WO) ........................ 435/6 |
| WO 97/10363 | * 3/1997 | (WO). |

OTHER PUBLICATIONS

Southern, E.M. "Detection of Specific Sequences Among DNA Fragments Separated by Gel Electrophoresis" *J. Mol. Biol.* 98:503–517 (1975).

Modrich, P. "Mismatch Repair, Genetic Stability, and Cancer" *Science* 266:1959–1960 (1994).

Su, S–S. and Modrich, P. "*Escherichia coli* mutS–Encoded Protein Binds to Mismatched DNA Base Pairs" *PNAS USA* 83:5057–5061 (1986).

Chang, D–Y. and Lu, A–L. "Base Mismatch–Specific Endonuclease Activity in Extracts from *Saccharomyces Cerevisiae*" *Nuc. Acids Res.* 19(17):4761–4766 (1991).

Yeh et al. "Two Nicking Enzyme Systems Specific for Mismatch–Containing DNA in Nuclear Extracts from Human Cells", *J. Biol. Chem.* 266(10):6480–6484 (1991).

Lee et al. "p53 and its 14 kDa C–Terminal Domain Recognize Primary DNA Damage in the Form of Insertion/Deletion Mismatches" *Cell* 81:1013–1020 (1995).

Youil et al. "Screening for Mutations by Enzyme Mismatch Cleavage with T4 Endonuclease VII" *PNAS USA* 92:97–91 (1995).

Mashal et al. "Detection of Mutations by Cleavage of DNA Heteroduplexes with Bacteriophage Resolvases" *Nature Genetics* 9:177–183 (1995).

Schena et al. "Parallel Human Genome Analysis: Microarray–Based Expression Monitoring of 1000 Genes" *PNAS USA* 93:10614–10619 (1996).

Miller, R.D. and Riblet, R. "Improved Phenol Emulsion DNA Reassociation Technique (PERT) Using Thermal Cycling" *Nucl. Acids Res.* 23(12):2339–2340 (1995).

Ellis et al. "MutS Binding Protects Heteroduplex DNA from Exonuclease Digestion In Vitro: A Simple Method for Detecting Mutations" *Nucl. Acids. Res.* 22(13):2710–11 (1994).

(List continued on next page.)

Primary Examiner—Lisa B. Arthur
Assistant Examiner—Jehanne Souaya
(74) *Attorney, Agent, or Firm*—Antoinette F. Konski; Deborah A. Dugan

(57) ABSTRACT

This invention provides various methods for identifying one or more genetic alterations in a sample polynucleotide strand.

21 Claims, 6 Drawing Sheets

OTHER PUBLICATIONS

Jiricny et al. "Mismatch–Containing Oligonucleotide Duplexes Bound by the *E.coli* mutS–Enchoded Protein" *Nucl. Acids Res.* 16(16):7843–53 (1988).

Lishanski et al. "Mutation Detection by Mismatch Binding Protein, MutS, in Amplified DNA: Application to the Cystic Fibrosis Gene" *PNAS USA* 91:2674–2678 (1994).

Su, S–S. and Modrich, P. "*Escherichia coli* mutS–Encoded Protein Binds to Mismatched DNA Base Pairs" *PNAS USA* 83:5057–61 (1986).

Rees et al. "Betaine Can Eliminate the Base Pair Composition Dependence of DNA Melting" *Biochemistry* 32:137–44 (1993).

Mayall, E. and Williams, C. "A Method for Routinely Extracting DNA from Buccal Cells for Cystic Fibrosis Carrier Screening" *J, Med. Genet.* 27:658 (1990).

Schuber et al. "A Simplified Procedure for Developing Multiplex PCRs" *Genome Research* 5:488–93 (1995).

Ørum et al. "Single Base Pair Mutation Analysis by PNA Directed PCR Clamping" *Nucl. Acids. Res.* 21(23):5332–36 (1993).

* cited by examiner

METHOD FOR DETECTING AND IDENTIFYING MUTATIONS

TECHNICAL FIELD

This invention is in the field of molecular biology and medicine. More specifically, it relates to methods of detecting and identifying mutations in nucleic acid sequences.

BACKGROUND

Genetic mutations are the primary cause of heritable disease and cancer. The genetic basis of disease, however, is complex and diverse, e.g., more than 700 presumed disease-causing mutations have been identified in the cystic fibrosis gene alone. Multiple mutations may be present in a single affected individual, and may be spaced within a few base pairs of each other, each of which may or may not be pathogenic. Thus, the ability to precisely locate and identify mutations is important for disease diagnosis, prediction, prevention and treatment.

Assays which detect the existence of nucleic acid mutations have been developed using various molecular biological techniques. One of the earliest methods involved the detection of restriction fragment length polymorphisms (RFLPs) using the Southern blotting technique. (Southern, E. M., *J. Mol. Biol.* 98:503–517 (1975)). RFLPs determine genetic variations in certain DNA fragments by cleaving the fragments with a type II restriction endonuclease. The differences in DNA length are due to the presence or absence of a specific endonuclease recognition site(s) and are detected using DNA hybridization with DNA probes after separation by gel electrophoresis.

Methods of detecting mutations which make use of polymerase chain reaction (PCR) have also been developed. In instances where the particular mutation has been identified, labeled primers can be used to determine whether a sample contains the known mutations. PCT/US93/04160 describes a method which allows perfectly matched DNA molecules to be separated from imperfectly matched molecules. The molecules can also be labeled to provide probes for identifying regions of heterozygosity in the genome.

In U.S. Pat. No. 5,217,863, Cotton et al. claims a method of detecting point mutations in sample DNA by hybridizing it to known DNA (without mutations) and subjecting the heteroduplex to hydroxylamine or osmium tetroxide and piperdine treatment. Hydroxylamine reacts with mismatched C and osmium tetroxide reacts with mismatched T (and to a lesser extent mismatched C), resulting in cleavage at the point of mismatch on addition of piperidine. The resulting material is then separated, for instance, by electrophoresis. If cleavage has occurred at one or more sites this will be apparent from the result of separation treatment, the number of fragments indicating the number of cleavages and hence the number of mutations of the type under consideration. However, the identity of the sequence(s) cannot be determined.

More recently, mutation-detecting assays have been developed that utilize proteins that recognize and bind to mismatched DNA heteroduplexes. (See, e.g., Modrich, *Science* 266:1959–1960 (1994) and U.S. Pat. No. 5,459,039). These proteins have been found in a variety of organisms in addition to *E. coli*. They act in concert to recognize and repair mismatches. In the simplest embodiment, heteroduplexes formed between reference and test DNAs are contacted with a mismatch recognition protein, such as MutS. The mixture is then passed over a nitrocellulose filter which binds the protein and any protein:DNA complexes. The presence of a mismatch in the contacted DNA is indicated by retention of the DNA:protein complex on nitrocellulose. However, this method indicates only the presence or absence of a mismatch, and does not directly allow for identification of the specific mutation(s).

Similarly, WO 95/12689, assigned to GeneCheck, Inc., describes contacting labeled heteroduplexed DNA with a labeled immobilized mismatch binding protein ("MBP") such as MutS. Binding, detected by direct or indirect methods, is indicative of a mismatch. Similarly, this method indicates only the presence or absence of a mismatch, and does not directly allow for identification of the specific mutation(s). Along the same vein, WO 93/02216, assigned to Upstate Biotechnology, Inc. describes how mutations can be detected using a labeled antibodies specific for MBPs to determine if a mismatch is present. Again, the identity of the mismatch is not determined.

Methods have also been described which determine the general location of a mismatch using mismatch binding proteins. (See, WO 95/29258) Here, a test strand of nucleic acid potentially containing a mutation is hybridized to a reference strand known not to have a mutation. The duplex is contacted with a MBP and the complex is then treated with an exonuclease. The digestion of the nucleic acid terminates at the position of any bound MBP. The relative sizes of the resulting degradation products are analyzed, for example by electrophoresis, to determine the presence and approximate location of the mismatch.

U.S. Pat. No. 5,459,039 to Modrich et al. describes a method for detecting base sequence differences between homologous regions of two DNA molecules. In this method, the two strands are annealed and a protein which recognizes mismatches is added to form a DNA:protein complex. Modrich describes several labor-intensive methods of "localizing" the mismatch. For example, single-stranded gaps near the mismatch can be generated by contacting the DNA:protein complex with a defined mismatch correction system. The DNA is then cleaved with a single-stranded specific endonuclease and at least one restriction enzyme. The electrophoretic mobilities of the fragments are then compared. Alternatively, heteroduplexed DNA containing at least one GATC sequence may be contacted with a mixture of mutS, mutL, and mutH. Cleavage of the DNA indicates presence of a mismatch. However, the position of the mismatch is not determined.

Alternatively, the location of the mismatch can be identified by chemically modifying at least one strand of the DNA duplex in the vicinity of the bound mismatch recognition protein. Modrich et al. describes how chemical modification, such as hydroxyl radical cleavage, can be accomplished by modifying the MutS protein to create a binding site for a metal ion which can catalyze formation of hydroxyl radicals which in turn will attack and cleave at least one strand of bound DNA in the vicinity of the mismatch.

Other methods of mismatch detection utilize chemical rather than enzymatic means. Chemicals that cleave at mismatched bases are also known. Osmium tetroxide, for instance, modifies mispaired thymidines while hydroxylamine modifies unpaired cytosines. Co-owned U.S. Pat. No. 5,217,863 describes how these chemically modified mismatches can be treated with piperdine, which results in elimination of the mismatched, modified nucleotide and breakage of one strand at the mismatch. Adapter-primer oligonucleotides are then ligated to the newly-created terminus followed by sequencing to identify the nucleotide sequence adjacent to the mismatch. However, the identity of the mismatched nucleotide(s) is not determined.

However, none of these methods directly identify the precise sequence of a mutation. Moreover, none of these methods provides for a high-throughput system for identifying unknown mutations. Currently, PCR amplification may be utilized to amplify region(s) of DNA, followed by sequencing of the PCR product(s). However, genes which are the loci of known disease-causing mutations may cover many kilobases of DNA. The cost and labor required to sequence every patient DNA sample over these important regions would make the detection of pathogenic mutations extremely slow and prohibitively expensive. Thus, one or more "mutation scanning" methodologies, such as those described above, is typically applied to detect the presence of mutations and limit the regions to be sequenced to those containing the potential alterations. This process is still time-consuming and laborious, since the scanning process does not aid in the subsequent process of sequence determination, which itself may pose separate and unique difficulties associated with template quality and quantity, as well as the inherent limitation of current methods to provide sequence in excess of a certain number of nucleotides from a primer (typically 600). Thus, a need exists which both indicates the presence of unknown mutations and which directly provides the sequence of the alteration(s). This invention satisfies these needs and provides related advantages as well.

SUMMARY OF THE INVENTION

This invention provides a method for identifying one or more genetic alterations in a sample polynucleotide strand by contacting the sample polynucleotide strand with a reference polynucleotide strand substantially homologous to the sample strand under conditions suitable to form a duplex of the sample and reference strands. The sequence may be in whole or in part, unknown. The duplexes are then contacted with an agent which recognizes and protects base pair mismatches under conditions which allow the agent to bind to the duplex at the mismatch to form a duplex:protein complex. Preferably, the agent is an MBP, a functional fragment, analog or variant, thereof. The complex is then contacted with an agent that removes unprotected base pairs such as a 3'→5' exonuclease to form a single-stranded region terminating at the position of the agent. To provide a unique position from which to sequence, the 3' terminus is then extended ("backfilled") to terminate at a position penultimate to the occurrence of a chosen nucleotide(s). This is performed using a DNA polymerase and a mixture of 2 or 3 different deoxynucleoside triphosphates. As will be apparent by the following discussion, this backfilling reaction is not required for identifying the presence of mutations. A partially-degenerate "adapter" oligonucleotide of predetermined sequence having the chosen nucleotide (as described above) at its 5' terminus is then ligated onto the sample strand. A primer complementary to a portion of the partially-degenerate oligonucleotide and a second primer complementary to a nucleotide sequence 5' to the region examined are then used to amplify the sample strand. Optionally, the sample polynucleotides can be separated from the reference polynucleotide prior to amplification to eliminate sequence information from the reference strand and to reduce assay "noise". Presence of a mutation is indicated by the production of an amplified product. The mutation is then identified by sequencing the product using standardized sequencing methods well known in the art.

This invention also provides a method for identification of one or more mutation(s) in a plurality of sample polynucleotides. The sample polynucleotides may have identical or non-identical sequences. The sequence may be in whole or in part, unknown. Duplexes are formed by contacting the sample polynucleotide strand with a reference polynucleotide strand substantially homologous to the sample strand under conditions suitable to form a duplex of the sample and reference strands. These duplexes are contacted by an agent which recognizes base pair mismatches under conditions which allow the agent to bind to the duplex at the mismatch to form a duplex:agent complex. Preferably, the agent is an MBP, a functional fragment, analog or variant, thereof. The mixture is digested with a 3'→5' exonuclease, and backfilled as described above. A single-stranded adapter oligonucleotide is then ligated to the duplex termini. The sample polynucleotides are then amplified using primers, the first (or "forward" primer) comprising a sequence complementary to the adapter oligonucleotide and the second, a set of "reverse" primers comprising sequence(s) 5' to the examined regions on the sample strands. Any amplified products which appear are sequenced to identify the mutuation. Optionally, the sample polynucleotides can be separated from the reference polynucleotide prior to amplification to eliminate sequence information from the reference strand and to reduce assay "noise".

This invention also provides a method for identifying one or more genetic alteration(s) in sample nucleotide strand by: (a) immobilizing the sample polynucleotide strand on one or more solid supports and contacting the sample polynucleotide strand with a reference polynucleotide strand substantially homologous to the sample strand under conditions suitable to form a duplex of the sample and reference strands; (b) contacting the duplex with an agent which recognizes and protects base pair mismatches under conditions which allow the agent to bind to the duplex at the mismatch to form a duplex:agent complex; (c) removing unprotected base pairs; (d) providing a unique base pair position from which to sequence; and (e) sequencing the sample polynucleotide strands to identify the genetic alteration(s).

This invention also provides a method for identification of one or more mutation(s) in sample polynucleotides by immobilizing a plurality of sample polynucleotides or reference polynucleotides on a single solid support. The sample polynucleotides may have identical or non-identical sequence. The sequence may be in whole or in part, unknown. Reference polynucleotides or sample polynucleotides (as appropriate) are then contacted with the immobilized polynucleotides to form reference:sample duplexes. As noted above, the sample polynucleotides may have identical or non-identical sequence. These duplexes are contacted by an agent which recognizes base pair mismatches under conditions which allow the agent to bind to the duplex at the mismatch to form a duplex:agent complex. Preferably, the agent is an MBP, a functional fragment, analog or variant, thereof. The complex is digested with a 3'–5' exonuclease, and backfilled as described above. A single-stranded adapter oligonucleotide is then ligated to the duplex termini. The sample polynucleotides are amplified using primers complementary to the adapter oligonucleotide and a sequence 5' to the examined region on the sample strand and sequenced to identify the mutation. Optionally, the sample polynucleotide can be separated from the reference polynucleotide prior to amplification to eliminate amplification of the reference strand DNA and reduce "noise."

In an alternative embodiment, the sequences of the polynucleotides may be in whole or in part, unknown. They may be comprised of PCR or multiplex (i.e., a plurality) of PCR products, restriction fragments, cDNA or other DNAs which are substantially double-stranded. The sample polynucleotides may have identical or non-identical sequence. A (set of) reference:sample duplex(es) is formed by contacting the sample polynucleotide strand with a reference polynucleotide strand substantially homologous to the sample strand under conditions suitable to form a duplex. If the polynucleotides are in excess of 1 kbp in size, the product duplex may be degraded by a double-strand cleaving activity to reduce the average size of the fragments. The duplexes are then contacted with an agent which recognizes and protects base pair mismatches under conditions which allow the agent to bind to the duplex at mismatches to form duplex:protein complex(es). Preferably, the agent is an MBP, a functional fragment, analog or variant, thereof. The complex is then contacted with an agent that removes unprotected base pairs such as a 5'→3' exonuclease to form a single-stranded region terminating at the position of the agent. The exonuclease is then removed or inactivated. A pair of "adapter" oligonucleotides of predetermined sequence, both having a short tract of degenerate sequence at their 3' ends are then ligated onto the digested sample strand 5' termini. The undigested single-stranded 3' overhangs left by the exonuclease (and the unligated adapters) are then degraded using a single-strand specific 3'→5' exonuclease. The "trimmed" 3' termini are then extended on the ligated adapter sequence template to produce a double-stranded product. A pair of primers complementary to portions of the fixed sequence element of each of the partially-degenerate adapters are then used to amplify both strands. Presence of a mutation is indicated by the production of an amplified product. The products are then cloned. The mutation(s) is then identified by sequencing the cloned product(s) using sequencing methods well known in the art.

As will become apparent, preferred features and characteristics of one aspect of the invention are applicable to any other aspect of the invention.

MODES FOR CARRYING OUT THE INVENTION

Figure 1A:
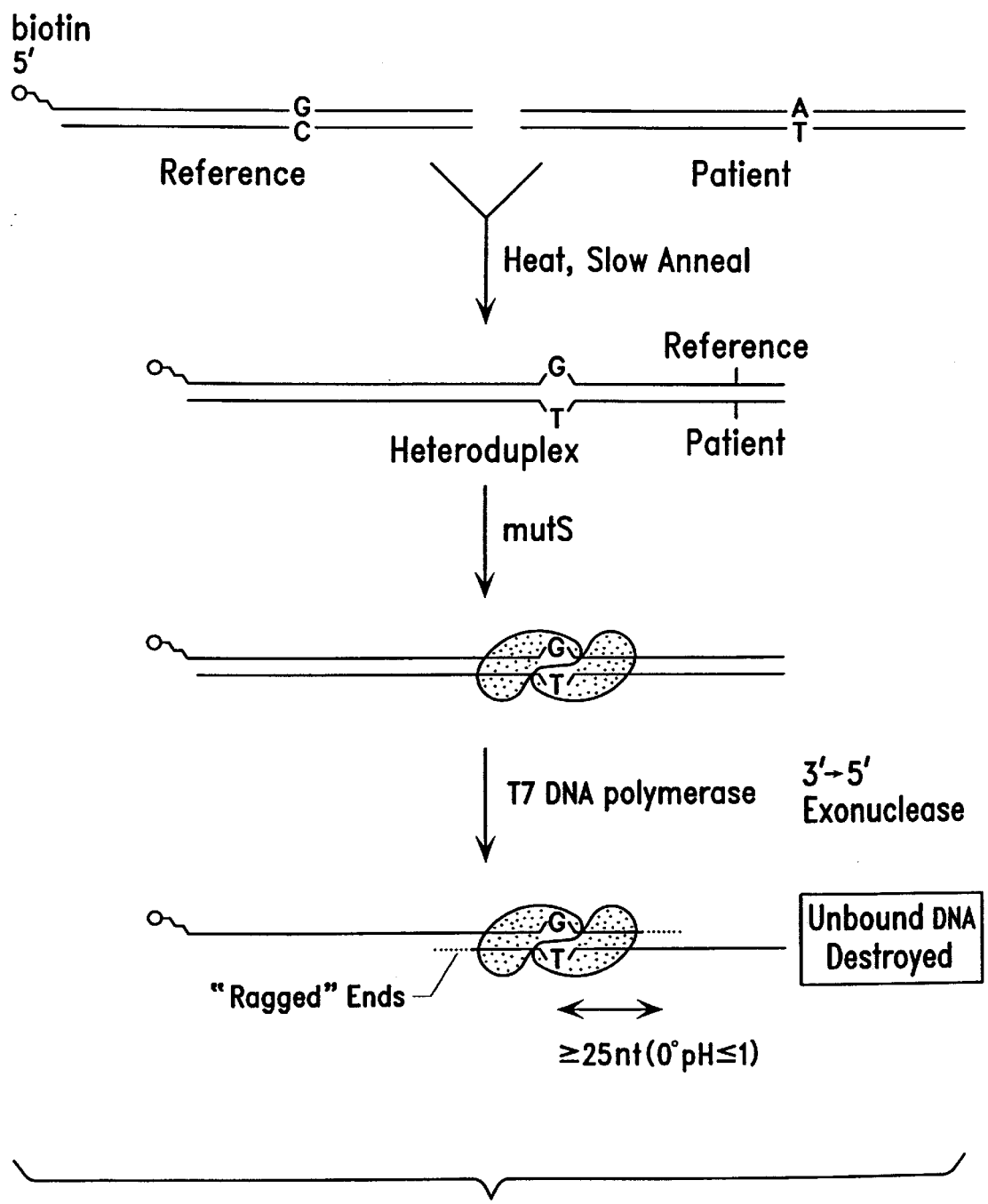
FIG. 1A is a schematic depicting the first steps of one embodiment of the present invention. A biotinylated reference DNA strand is annealed to sample DNA and the duplex contacted with a protein which recognizes mismatches, such as MutS. A 3'→5' exonuclease removes the nucleotides unprotected by the protein.

Throughout this application, various publications, patents, and published patent applications are referred to by an identifying citation. The disclosures of these publications, patents, and published patent specifications referenced in this application are hereby incorporated by reference into the present disclosure to more fully describe the state of the art to which this invention pertains.

The present invention is a method for directly identifying a mutation in a sample polynucleotide sequence. The method involves the use of at least one agent having the ability to specifically bind the mutated sequence under appropriate conditions. In other words, the agent has the ability to mask or protect the mismatch from degradation. In the preferred embodiment, the agent is a mismatch binding protein ("MBP"), a functional fragment, a functional analog or a functional variant thereof, or a mixture of different mismatch binding proteins, functional analogs or variants thereof.

Definitions

As used herein, certain terms will have specific meanings.

The terms "polynucleotide" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, know or unknown. The term "polynucleotide" includes single-, double-stranded and triple helical molecules. "Oligonucleotide" refers to polynucleotides of between about 6 and about 100 nucleotides of single- or double-stranded DNA or RNA. Oligonucleotides are also known as oligomers and may be isolated from genes, or chemically synthesized by methods known in the art. A "primer" refers to an oligonucleotide, usually single-stranded, that provides a 3'-hydroxyl end for the initiation of nucleic acid synthesis.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art, and include, but are not limited to, aziridinycytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudouracil, 5-pentylnyluracil and 2,6-diaminopurine. The use of uracil as a substitute for thymine in a deoxyribonucleic acid is also considered an analogous form of pyrimidine. These polynucleotides are intended to at least refer to the sample strand and the reference strand.

As used herein, "base pair," also designated "bp," refers to the complementary nucleic acid molecules; in DNA the purine adenine (A) is hydrogen bonded with the pyrimidine base thymine (T), and the purine guanine (G) with pyrimidine cytosine (C), also known as Watson-Crick base-pairing. A thousand base pairs is often called a kilobase, or kb. A "base pair mismatch" refers to a location in a nucleic acid molecule in which the bases are not complementary Watson-Cricks pairs.

The term "duplex" refers to the complex formed between two strands of hydrogen-bonded, complementary nucleic acid molecules. A duplex need not be entirely complementary, but can contain one or more mismatches or one or more deletions or additions. A duplex is sufficiently long-lasting to persist between formation of the duplex or complex and subsequent manipulations, including, for example, any optional washing steps.

As used herein, the term "reference strand" or "wild-type strand" refers to the nucleic acid molecule or polynucleotide having a sequence prevalent in the general population that is not associated with any disease or discernible phenotype. It is noted that in the general population, wild-type genes may include multiple prevalent versions that contain alterations in sequence relative to each other and yet do not cause a discernible pathological effect. These variations are designated "polymorphisms" or "allelic variations." It is therefore possible to prepare multiple reference strands, thereby providing a mixture of the most common polymorphisms. Alternatively, one reference strand may be used that has been selected for its particular sequence. The reference strand can also be chemically or enzymatically modified, for example to remove or add methyl groups. In one or more embodiments, the reference strand is comprised of a PCR product identical at least in part to the sequence prevalent in the general population. It is intended to include, but not be limited to polynucleotides as defined above, i.e., a gene or gene fragment, restriction fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers.

In a preferred embodiment, the reference strand or wild-type strand comprises a portion of a particular gene or genetic locus in the patient's genomic DNA known to be involved in a pathological condition or syndrome. Non-limiting examples of genetic syndromes include cystic fibrosis, sickle-cell anemia, thalassemias, Gaucher's disease, adenosine deaminase deficiency, alpha1-antitrypsin deficiency, Duchenne muscular dystrophy, familial hypercholesterolemia, fragile X syndrome, glucose-6-phosphate dehydrogenase deficiency, hemophilia A, Huntington disease, myotonic dystrophy, neurofibromatosis type 1, osteogensis imperfecta, phenylketonuria, retinoblastoma, Tay-Sachs disease, and Wilms tumor (Thompson and Thompson, *Genetics in Medicine*, 5th Ed.). It is intended to include, but not be limited to polynucleotides as defined above, i.e., a PCR product, a gene, a gene fragment, a restriction fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers.

In another embodiment, the reference strand comprises part of a particular gene or genetic locus that may not be known to be linked to a particular disease, but in which polymorphism is known or suspected. For example, obesity may be linked with variations in the apolipoprotein B gene, hypertension may be due to genetic variations in sodium or other transport systems, aortic aneurysms may be linked to variations in α-haptoglobin and cholesterol ester transfer protein, and alcoholism may be related to variant forms of alcohol dehydrogenase and mitochondrial aldehyde dehydrogenase. Furthermore, an individual's response to medicaments may be affected by variations in drug modification systems such as cytochrome P450s, and susceptibility to particular infectious diseases may also be influenced by genetic status. Finally, the methods of the present invention can be applied to HLA analysis for identity testing. It is intended to include, but not be limited to polynucleotides as defined above, i.e., a gene, a gene fragment, a restriction fragment, a PCR product, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers.

The term "sample strand" or "patient strand" refers to the polynucleotide having unknown sequence and potentially containing one or more mutations or mismatches as compared to the reference strand. This may be a PCR product amplified from patient DNA or other sample(s). It also is intended to include, but not be limited to polynucleotides as defined above, i.e., a gene, a gene fragment, a restriction fragment, a PCR product, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers.

In yet another embodiment, the reference strand comprises part of a foreign genetic sequence e.g. the genome of an invading microorganism. Non-limiting examples include bacteria and their phages, viruses, fungi, protozoa, myeoplasms, and the like. The present methods are particularly applicable when it is desired to distinguish between different variants or strains of a microorganism in order to choose appropriate therapeutic interventions.

The term "genetic alterations" or "mutations" is used to refer to a change from the wild-type or reference sequence of one or more nucleic acid molecules. It refers to base pair substitutions, additions and deletions of a sample strand when compared to a reference strand.

A linear sequence of polynucleotides is "substantially homologous" to another linear sequence, if both sequences are capable of hybridizing to form duplexes with the same complementary polynucleotide. Sequences that hybridize under conditions of high stringency are more preferred. These conditions are known in the art, see, e.g., Sambrook et al. (1989) MOLECULAR CLONING: A LABORATORY MANUAL, 2nd Edition, Cold Spring Harbor Press, N.Y. It is understood that hybridization reactions can accommodate insertions, deletions, and substitutions in the nucleotide sequence. Thus, linear sequences of nucleotides can be essentially identical even if some of the nucleotide residues do not precisely correspond or align. Preferably, the "substantially homologous" sample sequences of the invention contain a single mutation (mismatch) or an addition or deletion of 1 to about 10 base pairs when compared to the reference polynucleotide.

As used herein, the term "agent which recognizes and protects or masks the polynucleotide" from chemical or enzymatic degradation is any agent, proteinaceous or otherwise, which provides this functional activity when used in the method of this invention. In one embodiment, this agent is a mismatch binding protein or "MBP". MBP refers to the group of proteins which recognize and bind to nucleotide mismatches in polynucleotide duplexes. By recognizing and binding to improperly paired nucleotide strands, these proteins are involved in the complex pathway of genetic repair. Repair is generally initiated by the binding of the protein MutS to the mismatch. (See, Modrich (1994), supra). MutL then complexes with the MutS bound to the mismatch, which in turn complexes with MutH and leads to the activation of a GATC endonuclease associated with MutH. Cooperative action of MutS, MutL and DNA helicase (MutU) is required to remove the mismatch region, which is then repaired using polymerases and other enzymes.

"MBPs" includes several embodiments. These embodiments include any fragment, analog, mutein, variant or mixture thereof, which retains the ability to recognize and bind to a nucleotide mismatch. In one embodiment, a "variant" is a protein or polypeptide with conservative amino acid substitutions as compared to the wild-type amino acid sequence: the term therefore encompasses MutS and its homologues including hMSH2, hPMS 1, and hPMS2.

Mismatch repair proteins for use in the present invention may be derived from *E. coli* (as described above) or from any organism containing mismatch repair proteins with appropriate functional properties. Non-limiting examples of useful proteins include those derived from *Salmonella typhimurium* (MutS, see, Su, S. S. and Modrich, P., *Proc. Natl. Acad. Sci.* 84:5057–5061 (1986); MutL); *Streptococcus pneumoniae* (HexA, HexB); *Saccharomyces cerevisiae* ("all-type," MSH2, MLH1, MSH3); *Schizosaccharomyces pombe* (SWI4); mouse (rep 1, rep3); and human ("all-type," hMSH2, hMLH1, hPMS1, hPMS2, duc1). Preferably, the "all-type" mismatch repair system from human or yeast cells is used (Chang et al., *Nuc. Acids Res.* 19:4761 (1991); Yang et al., *J. Biol. Chem.* 266:6480 (1991)). In another embodiment, heteroduplexes formed between patients' DNA and wild-type DNA as described above are incubated with human "all-type" mismatch repair activity that is purified essentially as described in International Patent Application WO/93/20233. In another embodiment, heteroduplexes formed between patients' DNA and wild-type DNA as described above are incubated with p53 or its C-terminal domain (Lee, et al., Cell 81:1013–1020 (1995)).

When the agents are proteins or polypeptides, they can be in the L or D form so long as the biological activity of the polypeptide is maintained. For example, the protein can be altered so as to be secreted from the cell for recombinant production and purification. These also include proteins which are post-translationally modified by reactions that include glycosylation, acetylation and phosphorylation. Such polypeptides also include analogs, alleles and allelic variants which can contain amino acid derivatives or non-amino acid moieties that do not affect the biological or functional activity of the protein as compared to wild-type or naturally occurring protein. The term amino acid refers both to the naturally occurring amino acids and their derivatives, such as TyrMe and PheCl, as well as other moieties characterized by the presence of both an available carboxyl group and an amine group. Non-amino acid moieties which can be contained in such polypeptides include, for example, amino acid mimicking structures. Mimicking structures are those structures which exhibit substantially the same spatial arrangement of functional groups as amino acids but do not necessarily have both the $\alpha$-amino and $\alpha$-carboxyl groups characteristic of amino acids.

As used herein, the term "mismatch cleaving agent" refers to an enzyme or chemical agent which recognizes mismatched bases in polynucleotides and either causes cleavage of at least one strand or renders the polynucleotide susceptible to cleavage by another agent. Non-limiting examples of such agents include "resolvases" such as T4 endonuclease VII, (see Cotton et al., WO 9529251, Youil, et al., *Proc. Natl. Acad Sci.* 92:97–91 (1995)), CEL 1, and T7 endonuclease I (Mashal, et al., *Nature Genetics* 9:177–183 (1995)).

The term "exonuclease" refers to an enzyme that cleaves nucleotides sequentially from the free ends of a linear nucleic acid substrate. Exonucleases can be specific for double or single stranded nucleotides and/or directionally specific, for instance, $3' \rightarrow 5'$ and/or $5' \rightarrow 3'$. Some exonucleases exhibit other enzymatic activities, for example, native T7 DNA polymerase is both a polymerase and, in the absence of deoxynucleoside triphosphate, an active $3' \rightarrow 5'$ exonuclease. Exonuclease III removes nucleotides one at a time from the 3'-end of duplex DNA, exonuclease VII removes several nucleotides at a time from both ends of single-stranded DNA and lambda exonuclease removes nucleotides having attached 5' phosphate groups from the 5' end of duplex DNA.

The term "polymerase chain reaction" or "PCR" refers to a method for amplifying a DNA base sequence using a heat-stable polymerase such as Taq polymerase, and two oligonucleotide primers, one complementary to the (+)-strand at one end of the sequence to be amplified and the other complementary to the (−)-strand at the other end. Because the newly synthesized DNA strands can subsequently serve as additional templates for the same primer sequences, successive rounds of primer annealing, strand elongation, and dissociation can produce rapid and highly specific exponential amplification of the desired sequence. PCR also can be used to detect the existence of the defined sequence in a DNA sample.

As used herein a "solid support" refers to any support capable of binding the reference or sample nucleotides. Well-known supports include magnetic beads or other microparticles. Also useful are polyacrylamide, glass, natural cellulose, or modified cellulose such as nitrocellulose, polystyrene, polypropylene, polyethylene, dextran, or nylon. The solid support can have virtually any structure or configuration so long as it is capable of binding to the target strand. Methods of binding polynucleotide strands to solid supports are described, for example in U.S. Pat. No. 5,412,087 to McGall et al.; Shena et al. *PNAS USA* 93:10614–10619 (1996) and WO 95/35505.

Materials and Methods

Preparation of Sample and Reference Polynucleotides

Reference DNA can be synthesized by chemical means or, preferably, isolated from any organism by any method known in the art. The organism will have no discernible disease or phenotypic effects. This DNA may be obtained from any cell source, tissue source or body fluid. Non-limiting examples of cells sources available in clinical practice include blood cells, buccal cells, cerviovaginal cells, epithelial cells from urine, fetal cells, or any cells present in tissue obtained by biopsy. Body fluids include urine, blood, cerebrospinal fluid (CSF), and tissue exudates at the site of infection or inflammation. DNA is extracted from the cells or body fluid using any method known in the art. Preferably, at least 5 pg of DNA is extracted. The extracted DNA can be used without further modification or stored for future use.

Preferably, one or more specific regions in the extracted reference polynucleotide are amplified by PCR using a set of PCR primers complementary to genomic DNA separated by up to about 500 base pairs. PCR conditions found to be suitable are described below in the Examples. It will be understood that optimal PCR conditions can be readily determined by those skilled in the art. (See, e.g., *PCR 2: A PRACTICAL APPROACH* (1995) eds. M. J. McPherson, B. D. Hames and G. R. Taylor, IRL Press, Oxford).

PCR products can be purified by a variety of methods, including but not 5 limited to, microfiltration, dialysis, gel electrophoresis and the like. It is desirable to remove the polymerase used in PCR so that no new DNA synthesis can occur.

Duplex Formation

A reference:sample heteroduplex can be formed by any method of hybridization known in the art. In one embodiment, the reference and samples are separately heated and then annealed together. Preferably the heating step is between about 70° C. and about 100° C., more preferably between about 80° C. and 100° C., and even more preferably between about 90° C. and 100° C. The polynucleotide is kept at the elevated temperature for sufficient time to separate the strands, preferably between about 2 minutes and about 15 minutes, more preferably between about 2 and about 10 minutes and even more preferably about 5 minutes.

The separately heated reference and sample strands are then combined while at the elevated temperatures and allowed to cool. Generally, cooling occurs rather slowly, for instance the solution is allowed to cool to 50° C. over a period of about an hour. The cooling must be sufficiently slow as to allow formation of reference:sample duplexes including those with both high and low Tm. The duplexes can be used immediately, or stored at 4° C. until use.

Alternatively, a duplex can be formed by adjusting the salt and temperature to achieve suitable hybridization conditions. Hybridization reactions can be performed in solutions ranging from about 10 mM NaCl to about 600 mM NaCl, at temperatures ranging from about 37° C. to about 65° C. It will be understood that the stringency of the hybridization reaction is determined by both the salt concentration and the temperature. For instance, a hybridization performed in 10 mM salt at 37° C. may be of similar stringency to one performed in 500 mM salt at 65° C. In addition, organic solvents and/or chaotropic salts such as guanidine thiocyanate (2.5M) may be used, allowing hybridization to be performed at 37° C. Finally, means of accelerating hybridization such as phenol emulsion reassociation technique, or PERT (Miller & Riblet, *Nucl. Acids Res.* 23:2339–2340 (1995)) can be employed. For the present invention, any hybridization conditions can be used that form hybrids between substantially homologous complementary sequences, provided the reagents employed are compatible with the MBP and exonuclease employed. Generally, this can be accomplished by exchange into the reaction buffer of choice by dilution, extraction followed by ethanol precipitation, ultrafiltration or spin column chromatography and the like. In a preferred embodiment stringent hybridization conditions are used.

Binding to a Solid Support

Either the reference or patient strand may be bound to a solid support, either before or after addition of the mismatch binding protein. It is intended that the strand or duplex may be bound to the solid support at any point during the process(es) and it will be understood by the skilled artisan at what point or points during the process it is desirable to attach the strand or duplex to the solid support.

Non-limiting examples of matrices suitable for use in the present invention include nitrocellulose or nylon filters, glass beads, magnetic beads coated with agents for affinity capture, treated or untreated microtiter plates, and the like. It will be understood by a skilled artisan that the method by which the polynucleotide strand is bound to the solid support will depend on the particular solid support used. Amino-modified PCR products can be bound to silylated glass surfaces. (See, e.g., Schena et al, supra).

Suitable supports include, but are not limited to, beads or microtiter plates that are coated with a molecule capable of binding a polynucleotide to the solid support and which is compatible with this assay. Avidin can be used to bind a strand that has had biotin attached, for example by using biotin-conjugated PCR primers. In addition, antibodies can be used to attach the reference strand to any of the above mentioned solid supports by coating the surfaces with the antibodies and incorporating an antibody-specific hapten into the target DNA, e.g., digoxigenin, fluorescent dyes, eosin, DNP and the like. In a preferred embodiment, the reference or patient strand that has been amplified using biotinylated primers is bound to streptavidin-coated beads (CPG, Inc., Lincoln Park, N.J.). In one embodiment, the reference duplex is biotinylated at both 5' terminii. This significantly reduces noise, and allows detection of weak mismatches (i.e., C:C).

Mismatch Recognition

The reference:sample duplex is contacted with one or more agents having the ability to specifically bind to bp mismatches. This includes, but is not limited to, mismatch binding proteins. The agent is contacted under conditions which allow binding of the agent to the mismatch. Preferably, the MBP is *E. coli* MutS (Amershan Pharmacia Biotech) although other MBPs or mixtures of MBPs can be used. For instance, homologues of MutS such as MutS from *Thermus aquaticus* (Epicentre), *Streptococcus pneumoniae* HexA, hMSH2, genetically modified MutS or other mismatch binding proteins such as human p53, or genetically modified (non-cleaving forms) of mutY or RuvC proteins from *E. coli*, T7 endonuclease I or T4 endonuclease VII may be used. Preferably, the duplex is contacted with MutS at 0° C. for between about 10 and 30 minutes, preferably about 30 minutes. The pH of this step has a significant effect on the sensitivity of detection and the quality of the patterns obtained. At the pH which results in high affinity MutS binding (pH7.6 or above—see for example WO 95/29258; Ellis et al., *Nucl. Acids Res.* 22:2710–11; Jiricny et al., *Nucl. Acids Res.* 16:7843–53; Lishanski et al. *PNAS USA*

91:2674–8; Su and Modrich, *PNAS* 83:5057–61) the protection patterns obtained with the present invention consist of multiple bands for many mismatches. In addition, a strong preference for G:T mismatches is observed. In addition, the identity of the mismatched nucleotides makes a significant effect on the apparent position of MutS binding (see also Su and Modrich, supra). Lower pH values have been examined previously in MutS binding experiments, but have lead to high nonspecific binding (see Jiricny, et al., supra). Unexpectedly, however, at lower pH and especially below pH7.0, multiple bands in the present invention resolve into mostly single protected fragments which are more nearly identical for all mismatches protected. In addition, the yield of protected products becomes more similar between different mismatched nucleotide pairs. In addition, for some mismatches, binding below pH7.5 has been found to be necessary to observe any significant protection. Furthermore, the size of the protected fragments is also increased by performing binding (and protection) in lower pH. Thus, the pH of the MutS binding reaction is advantageously adjusted to near neutral pH, preferably between a pH of about 6.5 and 7.5, and more preferably, between a pH of about 6.5 and 7.0. A source of magnesium ions ($Mg^{++}$) can also be added to the reaction to enhance MutS binding. To produce more uniform protection patterns, a low concentration (1 $\mu$M) of ATP or a non-hydrolyzable ATP analog such as ATPγS can be added to the reaction.

Removing Unprotected Nucleotides, Back-Filling and Capture

When an agent such as a MBP binds to a mutation in a heteroduplex, it protects that portion of the DNA from chemical or enzymatic degradation. Similarly, the ends bound to a solid support, for instance by conjugation to a hapten, or otherwise protected will not be subject to degradation. Accordingly, in a preferred embodiment, after adding the MBP, an enzyme having exonuclease activity is added under conditions sufficient to remove nucleotides which are not bound by the MBP or coupled to a solid support. Preferably, a unidirectional exonuclease with high activity is used. In a preferred embodiment, the exonuclease is the 3'→5' exonuclease of T7 DNA polymerase and the DNA is digested for 3–5 minutes at 37° C. as shown in the bottom panel of the schematic of FIG. 1. The portion of the duplex bound by the MBP will be protected from exonuclease activity, thus the region of mismatch will remain double-stranded.

Figure 1B:
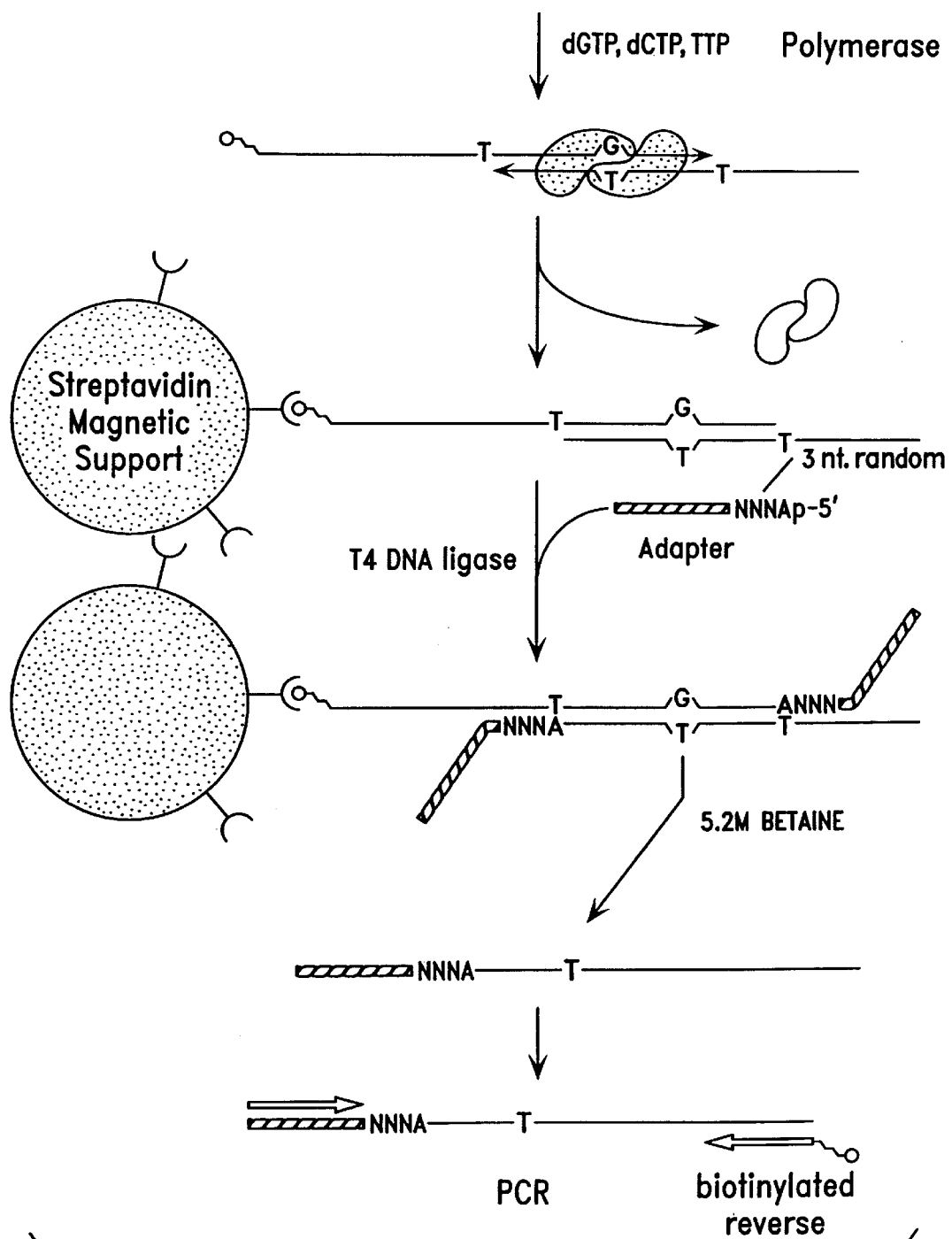
FIG. 1B is a schematic continuing from FIG. 1A. The exonuclease-generated 3' termini are extended by a DNA polymerase with a mixture of two or three deoxynucleoside triphosphates. The exonuclease-treated, polymerase filled DNA is captured on a solid support via biotin-avidin interactions. A partially degenerate adapter-primer is ligated to the 3' ends of the strands. The sample strand is dissociated from the reference strand. The sample strand is then amplified prior to sequencing using the adapter-complementary primer and the primer corresponding to the 5' end of the sample strand.
Figure 2:
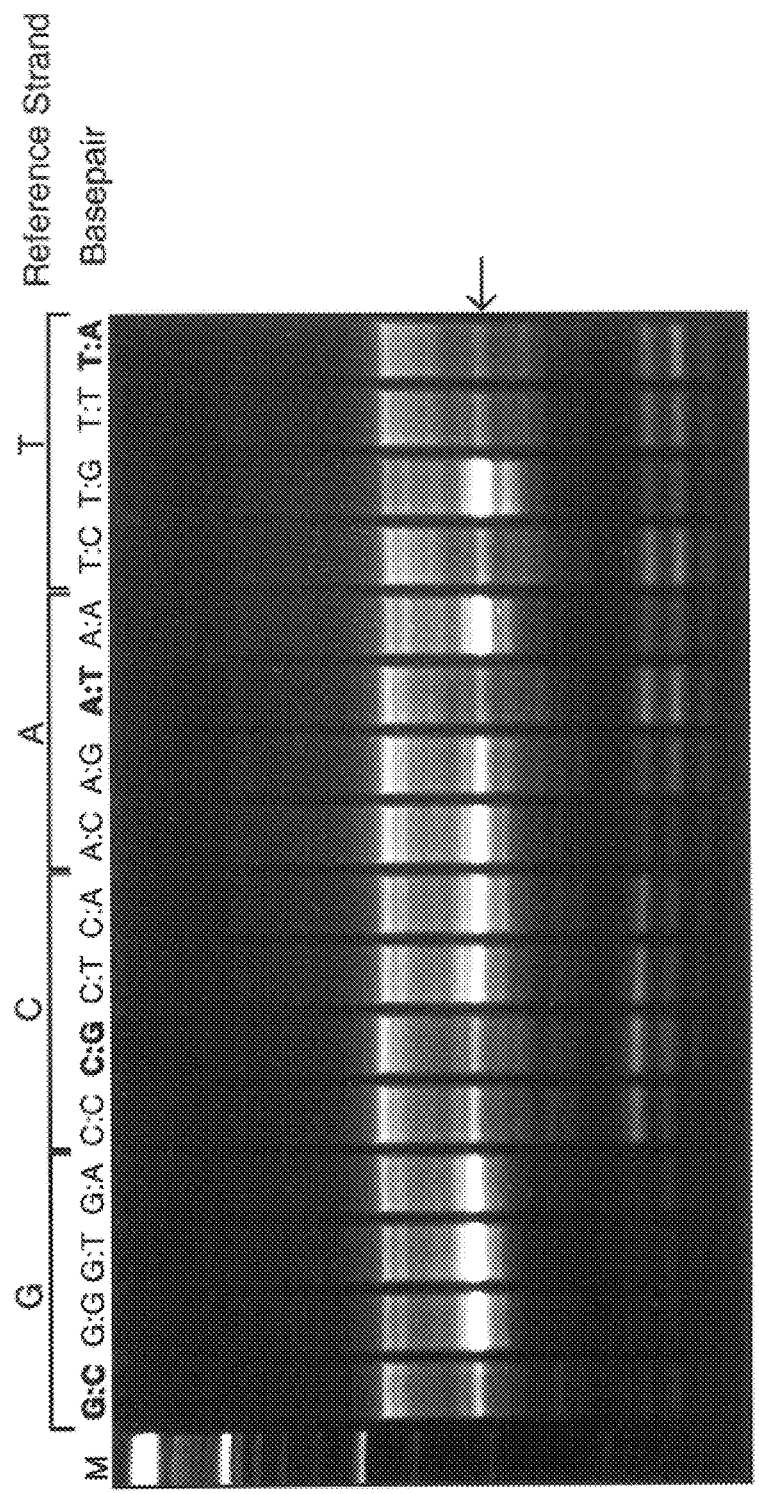
FIG. 2 is a photograph of an ethidium bromide stained agarose gel showing amplified protected fragments from a typical assay. A set of site-directed mutants in a 260 b.p. amplicon containing a portion of the cystic fibrosis transmembrane regulator exon 7 were assayed using mutS. "Reference Strand" indicates the nucleotide at position 154 of the amplicon which was present in the sense strand of the reference DNA. "Basepair" indicates the basepair formed at the same position with each of four non-biotinylated sample DNAs, each varying in the identity of the nucleotide at position 154.
Figure 3:
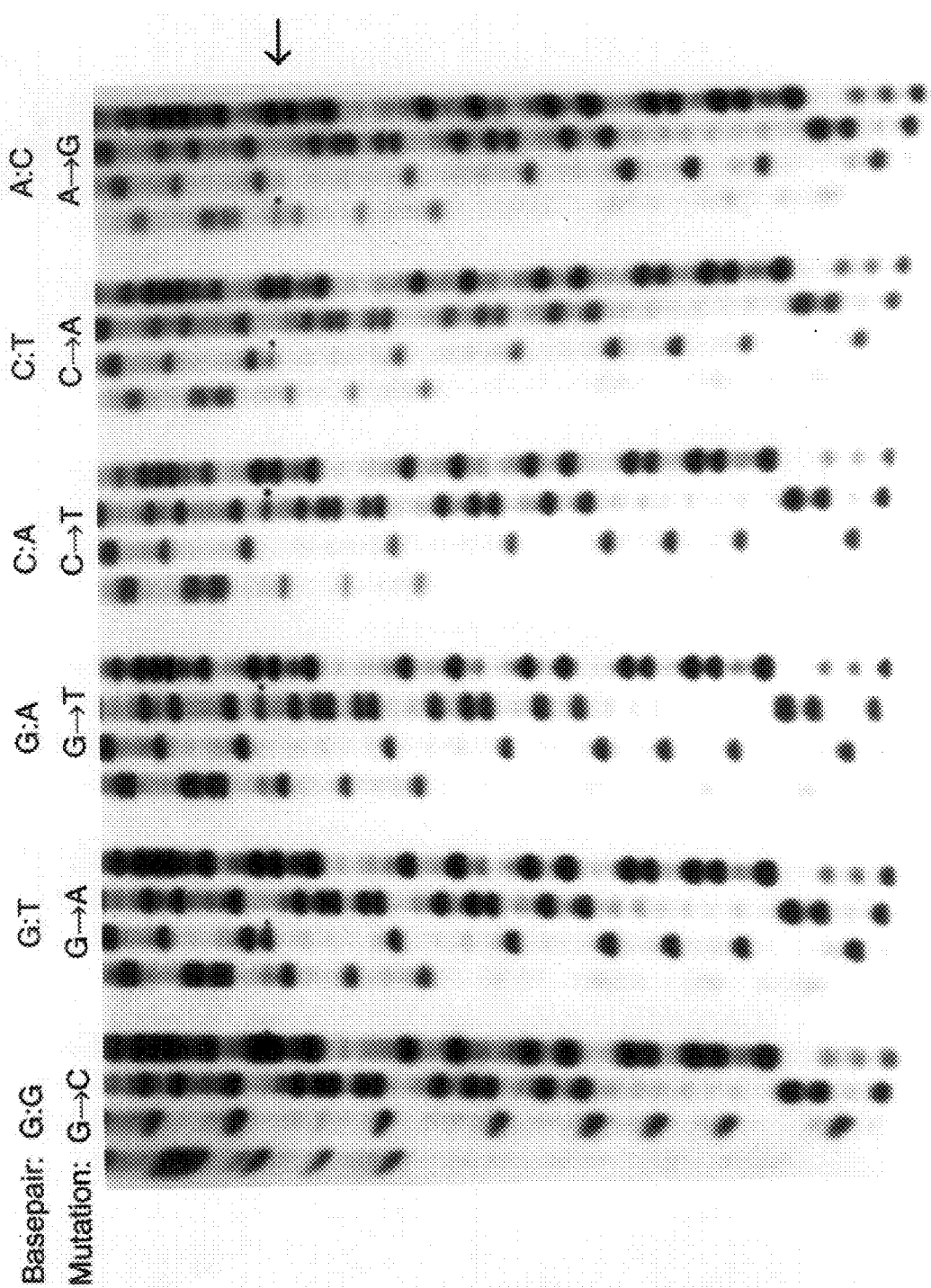
FIG. 3 is an autoradiograph of a sequencing experiment performed with amplified protected fragments excised from the gel shown in FIG. 2. The excised, recovered products were sequenced using an adapter-specific primer and $^{33}P$ dideoxynucleotides and Thermosequenase (Amersham). "Basepair" indicates the particular mismatch leading to the detected amplified product. "Mutation" indicates the nucleotide change leading to the particular mismatch shown. The arrow indicates the position corresponding to position 154 in the amplicon.
Figure 4A:
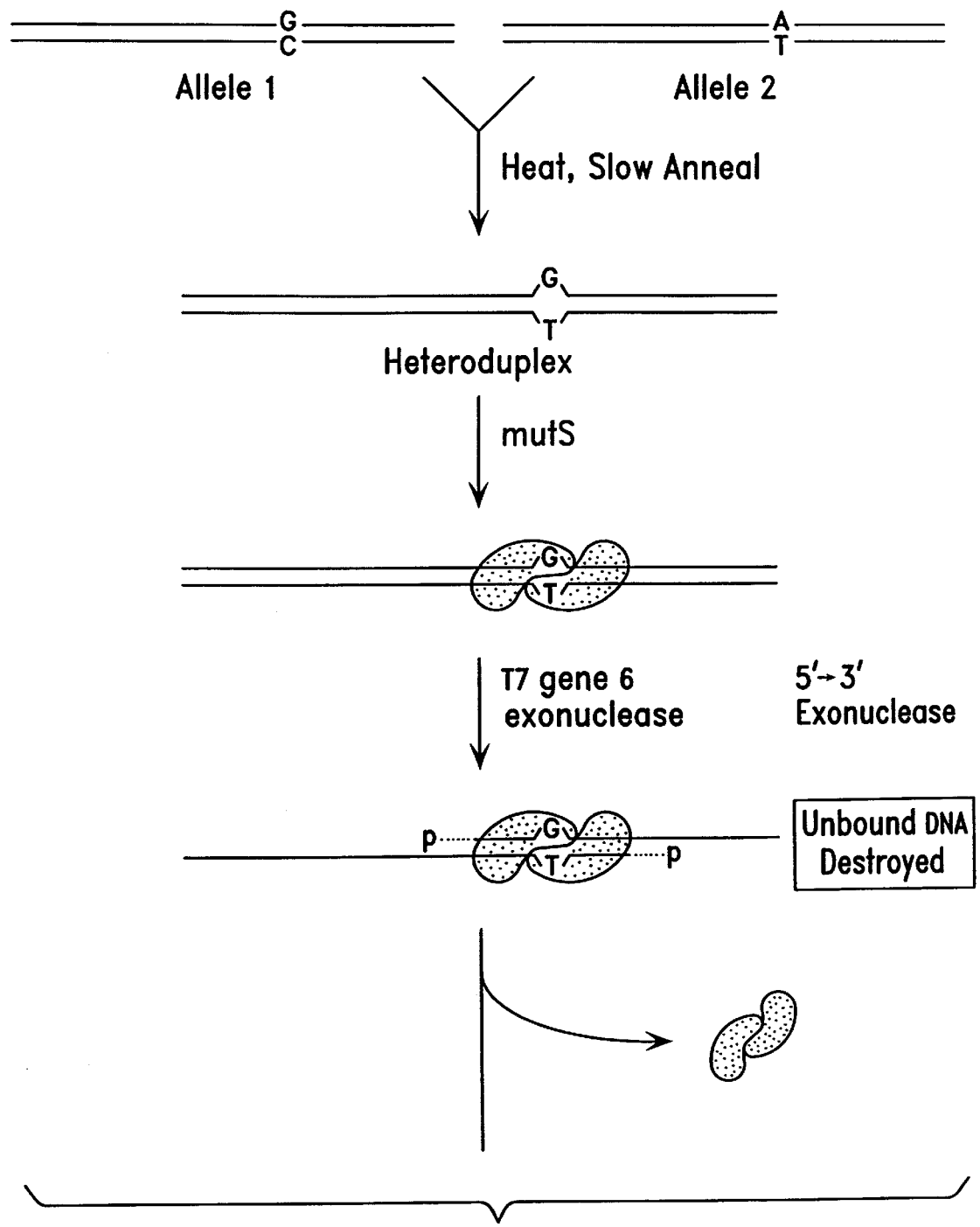
FIG. 4A is a schematic depicting the first steps of another embodiment of this invention. Two nucleic acid samples differing in sequence at one or more sites are heated and annealed to generate a heteroduplex DNA(s) containing mismatched nucleotides at the difference loci. The heteroduplex is contacted with MutS or other mismatch-binding protein. The complex is then contacted with a 5'→3' exonuclease such as T7 gene 6 exonuclease. The exonuclease is removed.
Figure 4B:
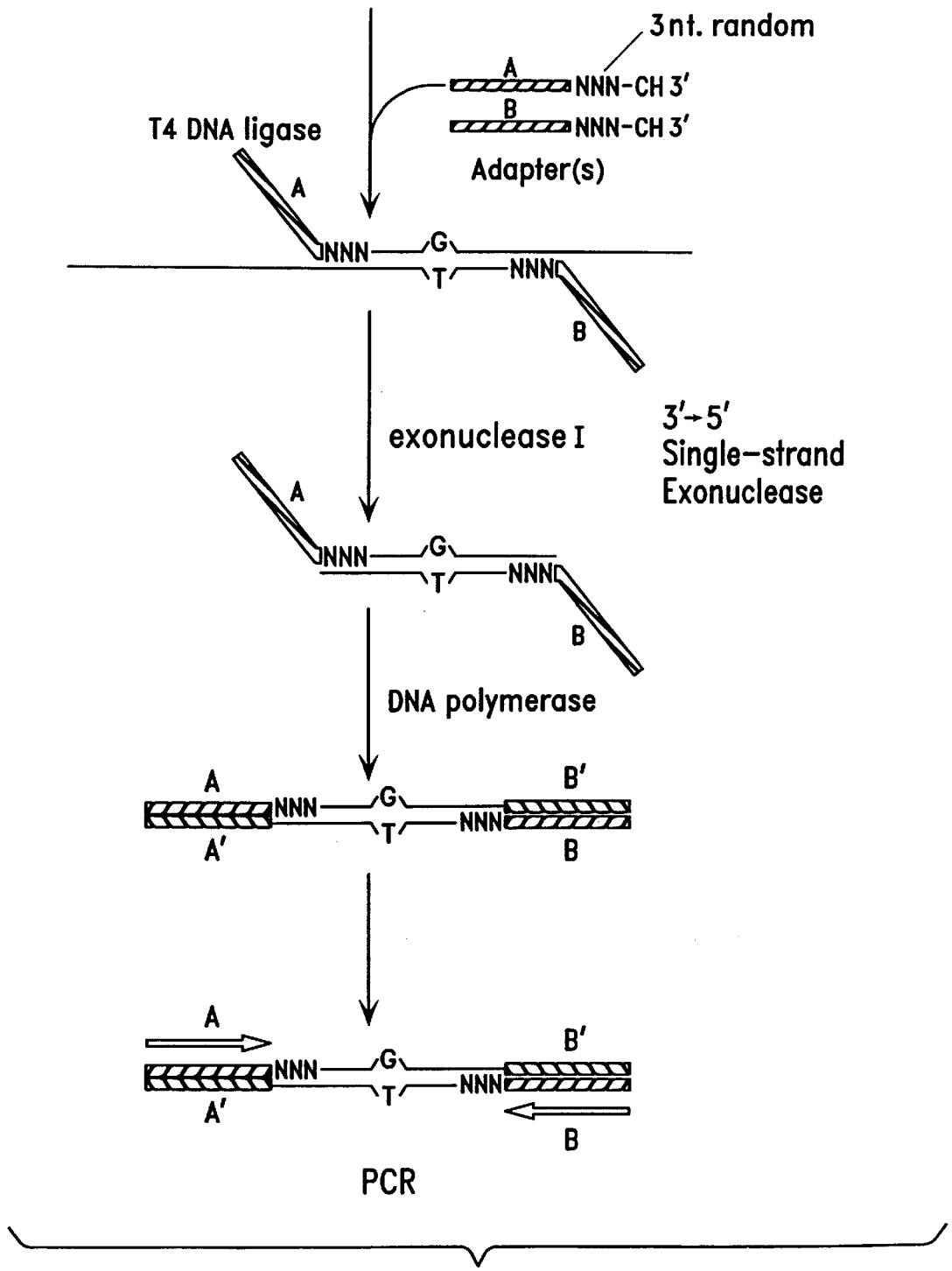
FIG. 4B is a schematic continuing from FIG. 4A. A 3'-partially-degenerate adapter oligonucleotide is ligated to the 5' ends of the strands. The product(s) are contacted with a single-strand-specific 3'→5' exonuclease such as exonuclease I. The newly-generated 3' termini are extended with a DNA polymerase to generate a full-duplex adapter sequence at each end. The product(s) is then amplified by PCR.

The top panel of FIG. 1B shows how oligonucleotides of predetermined sequence can be added onto each strand of duplex after exonuclease treatments. In one embodiment, the exonuclease is removed, then a mixture of three nucleoside triphosphates, preferably α-S-dGTP, α-S-dCTP, and α-S-TTP are added and the mixture incubated for about 5 minutes at 37° C. with an agent having DNA polymerase activity. The reaction is quenched for example, by addition of a high-salt buffer. Advantageously, this may be accomplished by direct capture of the products upon a solid support and washing, if the products are not already bound to the solid support, although other means may be utilized, such as deproteinization and ethanol precipitation, for example. Where the hapten is biotin, a preferred solid support is streptavidin attached to magnetic particles. Binding can be obtained by incubating the solid support and haptenylated duplex for about 30 minutes at room temperature.

Following exonuclease treatment and backfilling, the MBP may, in one embodiment, be removed. Any methods known in the art can be used to deproteinize the reference:sample duplex. Preferably, high salt conditions (or treatment with a protein denaturing reagent, such as a detergent) are used to remove the MBP. Alternatively, other known deproteinizing agents can be used to release the MBP.

Amplification and Mutated Sequence Determination

After removal of the MBP, the mutated sequence can be directly determined in a variety of ways. One embodiment is shown in FIGS. 1A and 1B. FIG. 1B shows how the washed, protein-free, backfilled, reference:sample duplex is contacted with a 5'-phosphorylated oligonucleotide (adapter) preferably having the sequence: 5'-pQZNNX, where N is an equimolar mixture of all four nucleotides, Q is any predetermined nucleotide, preferably A, and Z is any predetermined nucleotide or a mixture, preferably an equimolar mixture of all four nucleotides. X is sequence complementary to a primer having similar Tm as the primer (s) used to generate and analyze DNA, terminated with a blocking group such as a cordecypin (3' deoxyadenosine), phosphate, propyl group or the like. As shown in FIG. 1A, the sequence of the adapter is 5'-pANNNX.

Prior to ligation, the immobilized digested products can be incubated with single stranded DNAs or RNAs complementary to sequences within about 50 nucleotides 5' to the regions from which signals are undesirable. Due to inherent inaccuracies in chemical oligonucleotide synthesis and/or damage which is incurred during their synthesis, deprotection, or purification, significant nonspecific signal is generated from mismatches produced within the PCR primer sequences which can reduce assay sensitivity. These false signals may be advantageously blocked by incubation of the immobilized products with oligonucleotides complementary to the primer sequences prior to addition of the adapter and ligase.

At this point, FIG. 1B shows how the sample strand is separated from the reference strand for sequencing. Preferably, approximately 5 M betaine (N,N,N-trimethylglycine) is used for the elution of the sample strand ligation product. Betaine reduces background (noise) and minimizes the effect of that base composition surrounding the locus may have on the thermal stability of the duplex (see, for example, Rees, W. A., et al. Biochemistry (1993) 32:137–44) and thus on the ability to detect a sequence change. This compound also lowers the Tm of the polynucleotide duplexes (Rees, W. A., et al., supra.) enabling strand separation to be accomplished at room temperature. Other methods of releasing the sample strand can also be employed.

The released strand can then be directly amplified using a primer complementary to sequence X of the adapter and a second primer complementary to a sequence within the original DNA. The latter primer may be biotinylated to aid in the subsequent purification and sequencing of the product DNA. The amplified protected fragments can be resolved by electrophoresis in agarose or acrylamide gels or by other means such as HPLC, thin layer chromatography, size exclusion chromatography or capillary gel electrophoresis. The presence of amplified products of specific sizes by this analysis identifies samples which contain mutations or polymorphisms in the DNA. Each sequence alteration will produce a double-stranded DNA of unique size, thus allowing for the detection of more than one change in the sequence.

The amplified products, if present, may also be isolated and directly sequenced using a primer complementary to the adapter. Since each of the product DNAs are derived from patient DNA strand, only the mutant sequence is present. The expectation of only one sequence (as opposed to a mixture of mutant and normal sequence in the case of heterozygotes) also clearly distinguishes sequence alterations from sequencing ambiguities. Sequencing by extension of the primer complementary to the adapter usually places the mutation within 50 nucleotides. As will be recognized by those skilled in the art, sequencing close to the primer substantially improves the reliability of the sequence obtained. In addition, this approach also eliminates the need to separate (by cloning for example) mutant DNAs containing small deletions or insertions, which otherwise would generate nested sequences which pose difficulties in interpretation by direct sequence analysis.

Positional Cloning

The present invention offers an alternative, cost-effective method for localizing a disease-causing gene. Briefly, a polynucleotide from affected individuals is hybridized with a normal or wild-type polynucleotide as described above to form mismatch regions at the site of the mutation. Preferably, genomic DNA is digested with a restriction endonuclease which produces fragments on average several hundred nucleotides in size, although similar sized fragments of DNA corresponding to the chromosomal location may also be amplified from the patient's genomic DNA prior to inclusion in the hybridization reaction. Alternatively, larger genomic fragments may be utilized if the hybridization reaction is followed by treatment with an activity which cleaves both strands of the polynucleotide at opposing or nearly opposing positions. Such agents include restriction endonucleases, micrococcal nuclease, or DNase I in the presence of manganese ions. The hybrids are then treated in a protection experiment such as described above so that mismatch regions are recognized, bound and protected from digestion. There is no need to perform a "backfill" reaction. Any 5'→3' exonuclease may be utilized which is blocked by the binding of the MBP to the mismatch, including T7 gene 6 exonuclease or lambda exonuclease. The preferred exonuclease is T7 gene 6 exonuclease. A mixture of two oligonucleotide adapters of predetermined sequence are then ligated to the termini resulting from digestion. Any overhanging ends not subject to degradation by the exonuclease are then "trimmed" by a second 3'→5' single-strand specific exonuclease. Non-limiting examples may be exonuclease I (3'→5'), exonuclease VII (5'→3' and 3'→5'), or a DNA polymerase having exonuclease activity such as T4 or T7 DNA polymerase in the presence of nucleoside triphosphates. The preferred enzyme is exonuclease I. The "trimmed" termini generated by the second exonuclease are then extended with a DNA polymerase upon the ligated adapter template strands to copy the sequence of the second adapter into the 3' end of the protected product. The region with added adapter sequences is then amplified by PCR or other means. The products are then cloned. Finally, the sequence of the cloned DNA, which comprises the protected region in the vicinity of the mismatch is determined by methods well understood in the art.

It will be immediately understood by practitioners of the art that this approach will generate a large population of products from naturally-occurring but otherwise innocent variations in DNA sequence, referred to as polymorphisms. Such sequence variations will generate mismatches that are indistinguishable from disease-causing mutations. To eliminate these variations from the population, a variation of the method of "subtractive hybridization" (U.S. Pat. Nos. 5,436, 142 and 5,501,964) is performed. The mismatch binding-protection-amplification experiment is repeated with a pool of DNAs from unaffected individuals ("normal control" population) to generate a set of normal control probes. The primers to amplify this set are designed to not cross-hybridize with the primers used for amplification of the patient sample, and in addition contain one or more haptens, the preferred being biotin, which enable removal of the control probes and any sequences which can hybridize with them. The sample PCR products are mixed with an excess of normal control probe set, the mixture denatured by heating, reannealed, and those sequences hybridizing with the control probes removed by binding to a solid support bearing a hapten-binding moiety such as streptavidin. The unbound products are then reamplified utilizing the same set of primers used to amplify the patient sample. These products are then cloned and sequenced. It will be understood that the efficiency of hybridization and/or the abundance of naturally-occurring variants in the population may not be sufficiently high to remove all polymorphisms from the population of patient sample PCR products. To overcome this difficulty, the process may be repeated as many times as is required to select against polymorphic sequences. The process may be followed by conducting the experiment on DNA from an individual with a known mutation and following the abundance of the sequence in the PCR population by hybridization. Finally, the products can also be cloned in tandem arrays by including restrictions sites in the adapters which permit end-to-end ligation of the amplified protected fragment inserts prior to cloning (see, for example, SAGE patent WO 97/10363).

In this embodiment, determination of even a short sequence in the vicinity of the mismatch facilitates definitive identification of the disease-causing gene. The short sequence that is determined in the first round of sequencing can be used to design oligonucleotide probes for use in screening genomic or cDNA libraries. Other methods in which the primary sequence information can be used, either alone or in conjunction with library screening, include identification of tissue specific expression, reverse transcription-PCR amplification of mRNA, and screening of an affected population for genotype/phenotype association. Thus, without wishing to be bound by theory, it is contemplated that a previously unknown gene that causes a disease or other phenotype can be quickly and efficiently identified by these methods.

This invention also provides kits or reagent systems useful for practicing the methods described herein. Such a kit will contain a reagent combination comprising the essential elements required to conduct an assay as described herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and written instructions for the performance of assays. The kit of the present invention can include any configurations and compositions for performing the various assay formats described herein.

High-Throughput Screening

As is known in the art, high density arrays of bound nucleotides can be produced for high-throughput screening. The methods of the present invention are particularly suitable for high-throughput analysis of DNA, i.e., the rapid and simultaneous processing of DNA samples derived from a large number of patients. Furthermore, in contrast to other methods for de novo mutation detection, the methods of the present invention are suitable for the simultaneous analysis of a large number of genetic loci in a single reaction; this is designated "multiplex" analysis. Therefore, for any one sample or for a multiplicity of samples, the present invention allows the analysis of both intragenic loci (several regions within a single gene) and internecine loci (several regions within different genes) in a single reaction mixture. The manipulations involved in practicing the methods of the present invention lend themselves to automation, e.g., using multiwell microtiter dishes as a solid support or as a receptacle for, e.g., beads; robotics to perform sequential incubations and washes; and, finally, automated sequencing using commercially available automated DNA sequencers. It is contemplated that, in a clinical context, 500 patient DNA samples can be analyzed within 1–2 days in a cost-effective manner (less than $50.00/sample).

The following examples are intended only to illustrate the present invention and should in no way be construed as limiting the subject invention.

EXAMPLES

Example 1

Preparation of Sample DNA

Whole blood samples collected in high glucose ACD Vacutainers™ (yellow top) were centrifuged and the buffy coat collected. The white cells were lysed with two washes of a 10:1 (v/v) mixture of 14mM $NH_4Cl$ and 1 mM $NaHCO_3$, their nuclei were resuspended in nuclei-lysis buffer (10 mm Tris, pH 8.0, 0.4M NaCl,2 mM EDTA, 0.5% SDS, 500 µg/ml proteinase K) and incubated overnight at 37° C. Samples were then extracted with a one-fourth volume of saturated NaCl and the DNA was precipitated in ethanol. The DNA was then washed with 70% ethanol, dried, and dissolved in TE buffer (10 mM Tris-HCl, pH 7.5, 1 mM EDTA.)

Alternatively, Buccal cells were collected on a sterile cytology brush (Scientific Products) or female dacron swab (Medical Packaging Corp.) by twirling the brush or swab in the inner cheek for 30 seconds. DNA was prepared as follows, immediately or after storage at room temperature or at 4° C. The brush or swab was immersed in 600 µl of 50 mM NaOH contained in a polypropylene microcentrifuge tube and vortexed. The tube, still containing the brush or swab, was heated at 95° C. for 5 min, after which the brush or swab was carefully removed. The solution containing DNA was then neutralized with 60 µl of Tris, pH 8.0, and vortexed again (Mayall et al., *J. Med. Genet.* 27:658 (1990)). The DNA was stored at 4° C.

Example 2

Annealing of Reference and Sample Strands

The amplified sample DNA was separately heated and annealed in the presence of each biotinylated reference DNA. PCR products generated with Pfu DNA polymerase (Stratagene) were purified by deproteinization and sequential washing on a Centricon 100 filter (Amicon, Inc., Beverly Mass.). Five picomoles of each product DNA were mixed in 100 mM NaCl, 1 mM EDTA, 10 mM Tris•HCl pH7.5 and annealed by heating to 95° C. for 5 min. followed by slow cooling to 50° C. over a period of 90 min. (0.5° C. $min^{-1}$).

Example 3

Mismatch Recognition and Capture on a Solid Support

The annealed duplex (0.5 pmol total) was contacted with a mixture of 5 pmol of *E. coli* MutS protein (Amersham) and 5 pmol Taq MutS protein (Epicentre) on ice for 30 min. in 20 µl 7 mM $MgCl_2$, 5 mM DTT, 40 mM HEPES pH6.5. Ten units of T7 DNA polymerase was added and the DNA digested for 4 minutes at 37° C. A mixture of three nucleoside triphosphates, α-S-dGTP, α-S-dCTP and α-S-dTTP was added and the reaction incubated for 5 minutes at 37° C. High-salt buffer ("B&W": 1M NaCl, 10 mM Tris pH7.5, 1 mM EDTA, 0.1% Tween 80) was added to quench the reaction. The digested products were then captured by addition of 10 µl (100 µg) MPG streptavidin magnetic particles (CPG, Inc.) and incubation for 30 min. at room temperature. The particles were washed once with B&W buffer and once with ligation buffer (50 mM Tris pH7.5, 5 mM $MgCl_2$, 1 mM DTT, 100 µM ATP, and 100 µg/ml acetylated BSA).

Example 3b

Blocking of Primer-Generated Noise

After washing with ligation buffer, the particles with bound digest products were resuspended in 10 µl ligation buffer containing 50 pmol each of two oligonucleotides complementary to the primers used in the initial amplification. The mixtures were incubated for 5–10 minutes at room temperature.

Example 4

Ligation of Specific Primers and Sequencing

Following blocking, the products were contacted with a 5'-phosphorylated adapter having the sequence 5'-pANNNX, where N was an equimolar mixture of all four nucleotides and X was a sequence complementary to a primer having a similar Tm as the primer used to generate the sample strand. Ten (10) µl of ligation buffer containing 50 pmol of the oligonucleotide 5'-ANNNTGAGGCTGCGGACCGTGGGCCK (SEQ ID NO: 1), where K was a cordecypin (3' deoxyadenosine) residue and 5 Weiss units T4 DNA ligase was added and the mixture incubated for 30 min. at room temperature.

The ligated product was then washed by addition of 300 µl 0.3M NaCl, 50 mM Tris.HCl, pH7.5, 1 mM EDTA followed by separation and the sample strand (non-biotinylated) released by applying 50 µl of 5.2M betaine (N,N,N-trimethylglycine) solution and incubation for 10 minutes at room temperature. The sample strand (10 µl of the eluate) was then amplified using PCR with a primer complementary to sequence X of the ligated adapter sequence (5'-GGCCCACGGTCCGCAGCCTCA-3') (SEQ ID NO: 2) and a second primer complementary to a sequence within the strand. In some cases, the second primer was biotinylated to aid in the subsequent purification and sequencing of the sample strand.

The amplified products were resolved by agarose or acrylamide gels, or in some instances by HPLC or capillary gel electrophoresis. In the example shown, a 3% MetaPhor agarose gel was utilized. Because each genetic alteration produced a double-stranded DNA of a unique size, more than one change in the sequences could be detected.

Direct sequencing also can be performed. As is known in the art, PCR sequencing using suitable primers and labeled dideoxynucleotides can generate fragments which terminate at each base. These fragments can then separated by gel electrophoresis and the sequence determined.

Example 5

Mutation Identification/scanning Within a Known Genomic Region

A clone of the Sau3A fragment encompassing exon 7 of the CFTR gene incorporated in to the PCR product insertion site in pAT2.1 (InVitroGen) is cleaved with EcoRI to release the cloned insert, which is purified free of vector DNA by electrophoresis. One µg of the insert DNA is dephosphorylated for 60' with 0.1U calf intestinal phosphatase and deproteinized. Thiophospates are introduced into the 5' termni by incubation for 30 min. with 5U T4 polynucleotide kinase and 1 mM ATPγS in 50 mM Tris.HCl pH7.5, 10 mM MgCl$_2$, 1 mM DTT, and the unincorporated ATPγS removed by chromatography over a spin column of Sephadex G50 equilibrated with 50 mM HEPES pH7.5 1 mM EDTA. Biotins are added to the termini by addition of 1 mM 1-biotinamido-4-[4'-(maleimidomethyl)-cyclohexane-carboxamido]butane. ("Biotin-BMCC", Pierce) and incubation for 2 hours at room temperature. Unreacted reagent is removed by spin column chromatography, and the DNA quantitated by absorbance.

Patient DNA (10 µg) is digested to completion with Sau3A, and mixed with 0.5 picograms of biotinylated reference DNA in 1.5M sodium thiocyanate, 120 mM sodium phosphate pH6.8, 10 mM EDTA with 8% (v/v) freshly distilled phenol. The mixture is heated to 100° C. and chilled on ice. Heteroduplexes are formed by incubation in a thermal cycler at 37° C., while heating intermittently (every 15 min.) to 65° C. for two minutes for a total period of 24 h. The mixture is then extracted once with chloroform and chromatographed over a G50 Sephadex spin column to remove annealing buffer components.

One µg of the above heteroduplex DNA preparation is used in the same manner as the amplicon DNA as described in examples 3 and 4, except that the betaine eluate is amplified with PCR using a set of primers, the first member which is complementary to the adapter sequence (sequence 1 below) and the other complementary to sequence in either the 5' or 3' regions outside the exon boundaries, but within the Sau3A fragment sequence (sequences 2 and 3 below). The products appearing as bands which are distinguishable from samples from normal (control) DNA are excised and sequenced using a primer of the same sequence as sequence 1 below.

Sequence 1: 5'-GGC-CCA-CGG-TCC-GCA-GCC-TCA-3' (SEQ ID NO: 3) (adapter primer)

Sequence 2: 5'-CTC-AGA-CTC-CCA-GCC-CAA-AAA-TAA-AAT-AAC-ATC-CTG-AAT-3' (SEQ ID NO: 4) (5' to Exon 7)

Sequence 3: 5'-CTC-AGA-CTC-CCA-GCC-CTT-ACC-TGT-ATT-TTG-TTT-ATT-GCT-3' (SEQ ID NO: 5) (3' to Exon 7)

A 5' driver sequence (underlined) has been added to the primers 2 and 3 to permit amplification of the forward and reverse strand products under the same conditions (see Shuber, A. P. et al., Genome Research 5:488–93 (1995)).

Example 6

PNA Directed PCR Clamping for Suppression of Frequent Mutations/Polymorphisms

In some cases, it is advantageous to suppress signals arising from the occurance of common mutations and polymorphisms in same DNA(s). For example, a large fraction of patient samples suspected of containing mutant DNA sequences within the CFTR gene contain one ΔF508 allele. About 70% of the total mutant alleles in the population consist of ΔF508. Thus, when analyzing this gene, a signal corresponding to this mutation will frequently be found. Such signal(s) may in some cases interfere with detection of other mismatches within the same regions which are more weakly recognized by MutS. However, these signals may be selectively suppressed inclusion of a peptide nucleic acid (PNA) complementary to the allele in the PCR reaction (Orum, et al., Nucl. Acids. Res. 21:5332–36 (1993)).

Example 7

Positional Cloning of a Disease-causing Gene

The experiments described below are performed to rapidly localize and sequence a genomic region corresponding to a disease-causing gene. A multiplex family in which a genetic disease is expressed is identified using standard clinical indicators. DNA samples are obtained from affected and unaffected individuals as described above; if by patterns of transmission the disease appears to be an autosomal recessive syndrome, DNA samples are obtained from those individuals presumptively heterozygous for the disease gene.

DNA from heterozygous individual(s) prepared as described in example 1 is digested with Alu I, heat denatured and self-annealed. Ten micrograms of Alu-digested genomic DNA is heated to 100° C. for 10 min. in 50 µl 1.5M sodium thiocyanate, 120 mM sodium phosphate pH6.8, 10 mM EDTA and 8% freshly-distilled phenol. The mixture is chilled on ice, and then placed in the thermal cycler and cycled for 2 min. at 65° C. followed by 15 min. at 37° C. for 24 h. The mixture is then chromatographed over a Sephadex G50 spin column (Pharmacia). A mixture of Taq and E. coli mutS (10 pmol each) is added to 1 µg of the eluted DNA in 50 mM HEPES pH7.2, 7 mM MgCl2, 1 mM DTT, and the mixture incubated 30 min on ice. The mixture is then digested with 20 units T7 gene 6 exonuclease (Amersham) for 15 min at 37° C. The reaction is quenched by phenol extraction and chromatography over Sephadex G50. Two oligonucleotide adapters having the sequences (1) 5'-HO-GGCCCACGGTCCGAAGACCTCNNN-OH-3' and (SEQ ID NO: 6) (2) 5'-HO-GGGCCGGACCGGATGGGATCANNN-OH'-3' (SEQ ID NO: 7) are ligated to the DNA digest in 50 mM Tris.HCl, 10 mM MgCl2, 1 mM ATP and 1 mM DTT with 5 Weiss units T4 DNA ligase at room temperature for 1 hr. To remove overhanging ends left by the T7 exonuclease, 100 units exonuclease I (Amersham) are added, and the mixture incubated for 30 min at 37°. The products are rendered fully double-stranded by incubation with 5 units T4 DNA polymerase, and 200 µM each dATP, dGTP, dCTP, and TTP for 10 min at 37°. The mixture is then heated to inactivate any residual exonuclease, and amplified by PCR utilizing primers identical to the sequences above, except lacking the 3' degenerate nucleotides (Primer Set 1).

A separate parallel experiment is performed with pooled genomic DNA from a control population of individuals suspected of being free of genetic defects in the selected gene, but otherwise being similar to the heterozygous sample by way of national origin, race, or other distinguishing characteristics known to represent a source of variation in the frequency of the disease. In this case, the final amplification is performed with primers (Primer Set 2) which will not crosshybridize with the primers used for the heterozygous DNA. This set of products is biotinylated either by introduction of biotin into the primers or following PCR by tailing with biotinylated deoxynucleoside triphosphates and TdT. The products are hybridized to the products of the heterozygote PCR, and material annealing to the control products is removed by adsorption to streptavidin agarose. After hybridization and chromatography (described above), the samples are incubated with 50 µg streptavidin agarose (Life Technologies, Inc.) for 30 min at room temperature in 1M NaCl, 10 mM Tris, 1 mM EDTA pH7.5. The unbound material is recovered by G50 spin column chromatography. This "subtracted" library is reamplified using primer set 1, and the subtraction and amplification steps performed one additional time. Finally, the products are cloned into appropriate vectors and the products sequenced. This may advantageously be performed by first ligating the sequences into tandem arrays (preferably of 600 nucleotides) allowing high-throughput analysis of the sequences. Mutations are identified by isolation of two alleles differing by only limited sequence changes (transitions, transversions, and deletion/insertions of up to 3 nucleotides). A set of allele-specific oligonucleotides designed to hybridize and distinguish the two alleles can then be utilized to perform segregation analysis in families of affected individuals. The DNA from identified clones is then used to screen cDNA libraries, and may be used to extract genomic DNA fragments, messenger RNA or cDNA prior to cloning and screening.

It is to be understood that while the invention has been described in conjunction with the above embodiments, that the foregoing description and the following examples are intended to illustrate and not limit the scope of the invention.

Other aspects, advantages and modifications within the scope of the invention will be apparent to those skilled in the art to which the invention pertains.

What is claimed is:

1. A method for identifying one or more genetic alterations in a sample polynucleotide strand, comprising:
   (a) providing a duplex comprising the sample polynucleotide strand and a reference polynucleotide strand;
   (b) contacting the duplex with an agent which recognizes and protects base pair mismatches under conditions which allow the agent to bind to and protect the duplex at the mismatch to form a duplex:agent complex;
   (c) removing unprotected base pairs;
   (d) providing a preselected site from which to sequence; and
   (e) determining the sequence of the sample strand to identify the one or more genetic alterations in the sample polynucleotide strand.

2. The method according to claim 1, wherein step (d) comprises contacting the duplex with an agent having DNA polymerase activity and a mixture of 2 to 3 different deoxynucleoside triphosphates.

3. The method according to claim 1, wherein step (d) comprises ligating an adapter oligonucleotide to the sample stand.

4. The method according to claim 1 which further comprises step (a)(i), which comprises immobilizing the duplex to a solid support.

5. A method for identifying one or more genetic alterations in a sample polynucleotide strand, comprising:
   (a) providing a plurality of duplexes, wherein each duplex comprises a sample polynucleotide strand and a reference polynucleotide strand;
   (b) contacting the duplexes with an agent which recognizes and protects base pair mismatches under conditions which allow the agent to bind to and protect the duplexes at the mismatch to form duplex:agent complexes;
   (c) removing unprotected base pairs;
   (d) providing a preselected site from which to sequence; and
   (e) determining the sequence of the sample strands to identify the one or more genetic alterations in the sample polynucleotide strands.

6. The method according to claim 5, wherein step (d) comprises contacting the duplexes with an agent having DNA polymerase activity and a mixture of 2 to 3 different deoxynucleoside triphosphates.

7. The method according to claim 5, wherein step (d) comprises ligating an adapter oligonucleotide to the sample stands.

8. The method according to claim 5, which further comprises step (a)(i), which comprises immobilizing the duplex to a solid support.

9. A method for identifying one or more genetic alteration (s) in a sample nucleotide strand comprising:
   (a) providing a duplex by immobilizing the sample polynucleotide strand on one or more solid supports and contacting the sample polynucleotide strand with a reference polynucleotide strand under conditions suitable to form a duplex between the sample and reference strands;
   (b) contacting the duplex with an agent which recognizes and protects base pair mismatches under conditions which allow the agent to bind to and protect the duplex at the mismatch to form a duplex:agent complex;
   (c) removing unprotected base pairs;
   (d) providing a preselected site from which to sequence; and
   (e) sequencing the sample polynucleotide strands to identify the one or more genetic alteration(s).

10. The method according to claim 9, wherein step (d) comprises contacting the duplex with an agent having DNA polymerase activity and a mixture of 2 to 3 different deoxynucleoside triphosphates.

11. The method according to claim 9, wherein step (d) comprises ligating an adapter oligonucleotide to the sample stand.

12. A method for identifying one or more genetic alteration(s) in one or more sample polynucleotide strands comprising:
   (a) providing a plurality of duplexes by immobilizing a plurality of sample polynucleotide strands on one or more solid supports and contacting the plurality of sample polynucleotide strands with a reference polynucleotide strand under conditions suitable to form a duplex between the sample and reference strands;
   (b) contacting the duplex with an agent which recognizes and protects base pair mismatches under conditions which allow the agent to bind to and protect the duplex at the mismatch to form a duplex:agent complex;
   (c) removing unprotected base pairs;
   (d) providing a preselected site from which to sequence; and sequencing the sample polynucleotide strands to identify the alteration(s).

13. The method according to claim 12, wherein step (d) comprises contacting the duplex with an agent having DNA polymerase activity and a mixture of 2 to 3 different deoxynucleoside triphosphates.

14. The method according to claim 12, wherein step (d) comprises ligating an adapter oligonucleotide to the sample stand.

15. The method according to any of claims 1, 5, 9 or 12, wherein step (d) comprises ligating two adapter oligonucleotides to the product(s) of step (c).

16. The method according to claim 15, wherein the two adapter oligonucleotides are single-stranded.

17. The method according to claim 15, wherein following ligation of the adapter oligonucleotides, any remaining strands are degraded and extended upon the adapter template to produce a double-stranded products.

18. The method according to any of claims 1, 5, 9 or 12, wherein the agent is MutS.

19. The method according to any of claims 1, 5, 9 or 12, wherein the reference strand further comprises a biotin or analog thereof at the 5' termini.

20. The method according to any of claims 1, 5, 9 or 12, wherein the reference strand is selected from the group consisting of a PCR product, a multiplex restriction product, a cDNA, and a mRNA.

21. The method according to any of claims 1, 5, 9 or 12, wherein the sample strand is selected from the group consisting of a PCR product, a multiplex restriction product, a cDNA, and a mRNA.

* * * * *

SEQUENCE LISTING

```
<160> NUMBER OF SEQ ID NOS: 7

<210> SEQ ID NO 1
<211> LENGTH: 26
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (2)...(2)
<223> OTHER INFORMATION: n is any nucleotide
<220> FEATURE:
<221> NAME/KEY: misc_feature
<222> LOCATION: (3)...(3)
<223> OTHER INFORMATION: n is any nucleotide
<220> FEATURE:
<221> NAME/KEY: misc_feature
<222> LOCATION: (4)...(4)
<223> OTHER INFORMATION: n is any nucleotide
<220> FEATURE:
<221> NAME/KEY: misc_feature
<222> LOCATION: (26)...(26)
<223> OTHER INFORMATION: n is a cordycepin residue

<400> SEQUENCE: 1
annntgaggc tgcggaccgt gggccn                                    26

<210> SEQ ID NO 2
<211> LENGTH: 21
<212> TYPE: DNA
<213> ORGANISM: Unknown
<220> FEATURE:
<223> OTHER INFORMATION: Primer

<400> SEQUENCE: 2
ggcccacggt ccgcagcctc a                                         21

<210> SEQ ID NO 3
<211> LENGTH: 21
<212> TYPE: DNA
<213> ORGANISM: Unknown
<220> FEATURE:
<223> OTHER INFORMATION: Primer

<400> SEQUENCE: 3
ggcccacggt ccgcagcctc a                                         21

<210> SEQ ID NO 4
<211> LENGTH: 39
<212> TYPE: DNA
<213> ORGANISM: Unknown
<220> FEATURE:
```

```
<223> OTHER INFORMATION: Primer

<400> SEQUENCE: 4
ctcagactcc cagcccaaaa ataaaataac atcctgaat                              39

<210> SEQ ID NO 5
<211> LENGTH: 39
<212> TYPE: DNA
<213> ORGANISM: Unknown
<220> FEATURE:
<223> OTHER INFORMATION: Primer

<400> SEQUENCE: 5
ctcagactcc cagcccttac ctgtattttg tttattgct                              39

<210> SEQ ID NO 6
<211> LENGTH: 24
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (22)...(22)
<223> OTHER INFORMATION: n is any nucleotide
<220> FEATURE:
<221> NAME/KEY: misc_feature
<222> LOCATION: (23)...(23)
<223> OTHER INFORMATION: n is any nucleotide
<220> FEATURE:
<221> NAME/KEY: misc_feature
<222> LOCATION: (24)...(24)
<223> OTHER INFORMATION: n is any nucleotide

<400> SEQUENCE: 6
ggcccacggt ccgaagacct cnnn                                             24

<210> SEQ ID NO 7
<211> LENGTH: 24
<212> TYPE: DNA
<213> ORGANISM: Unknown
<220> FEATURE:
<223> OTHER INFORMATION: Primer
<220> FEATURE:
<221> NAME/KEY: misc_feature
<222> LOCATION: (22)...(22)
<223> OTHER INFORMATION: n is any nucleotide
<220> FEATURE:
<221> NAME/KEY: misc_feature
<222> LOCATION: (23)...(23)
<223> OTHER INFORMATION: n is any nucleotide
<220> FEATURE:
<221> NAME/KEY: misc_feature
<222> LOCATION: (24)...(24)
<223> OTHER INFORMATION: n is any nucleotide

<400> SEQUENCE: 7
gggccggacc ggatgggatc annn                                             24
```